United States Patent [19]
Hyman

[11] 3,968,803
[45] July 13, 1976

[54] SURGICAL CHEST DRESSING

[75] Inventor: Davie S. Hyman, Gates Mills, Ohio

[73] Assignee: Golda, Inc., Cleveland Heights, Ohio

[22] Filed: June 4, 1975

[21] Appl. No.: 583,785

[52] U.S. Cl. ............................... 128/482; 128/157
[51] Int. Cl.² ..................... A41C 3/02; A61F 13/00
[58] Field of Search ......................... 128/155–157, 128/482, 488, 503, 510, DIG. 15, 78

[56] References Cited
UNITED STATES PATENTS

| | | | |
|---|---|---|---|
| 2,443,127 | 6/1948 | Abeles | 128/482 X |
| 2,662,522 | 12/1953 | Muller | 128/155 |
| 2,800,902 | 7/1957 | Wiltrout | 128/482 |
| 3,399,669 | 9/1968 | Kaplan | 128/78 |
| 3,561,442 | 2/1971 | Goswitz | 128/157 |

FOREIGN PATENTS OR APPLICATIONS

| | | | |
|---|---|---|---|
| 1,156,910 | 12/1957 | France | 128/482 |
| 597,485 | 1/1948 | United Kingdom | 128/482 |

Primary Examiner—Lawrence W. Trapp

[57] ABSTRACT

A surgical chest dressing comprising a chest encircling flexible band having a longitudinally continuous back portion adapted to lie against the back of a person using the dressing. The continuous back portion has two longitudinally spaced ends with each of the ends connected to one of a pair of front flaps which include two ends spaced from the back portion and overlapping each other at engaging surfaces when the dressing is wrapped around a person using the same. A two element, contact sensitive, reusable fastening means is used for releasably securing the free ends together in selected, adjustable longitudinal positions. The dressing also includes first and second straps which are fixedly secured onto the back portion and coact with means on the front flaps for securing the straps in place and holding the dressing in the proper supporting position.

10 Claims, 5 Drawing Figures

SURGICAL CHEST DRESSING

This invention relates to the art of surgical dressings and more particularly to an improved chest dressing.

The invention is particularly applicable for a surgical chest dressing for use on a mastectomy patient and it will be described with particular reference thereto; however, it has much broader applications and may be used for post-operative dressings of various chest surgery patients.

After a mastectomy operation, it is beneficial to make the patient as comfortable and normal feeling as possible under the circumstances. In the past, the patient was bandaged by absorbent material over the closed incision and an elastic band wrapped around the chest of the patient to hold the dressing in place. This elastic band distorted the un-operated breast and somewhat restricted the ability of the patient to experience normal respiration involving an expansion and contraction of the chest. In addition, such bandaging required disruption of the anesthetic apparatus and disconnection of any tubes directed to intravenous needles being used to administer drugs. The patient had to be lifted and held in the lifted position until the wrap was concluded. After the operation, the patient experienced substantial difficulty and was heavily bandaged causing discomfort and some emotional strain. In addition, when the dressing was to be changed, it was a complex procedure which could not be done efficiently by the patient or by an untrained person.

Several efforts have been made to overcome the disadvantages of the bandaging explained above. However, these prior attempts have involved the use of elastic bandaging which is used to hold the dressing in place. In some instances, metal clips and fasteners were used to secure the bandage around the chest of a post mastectomy patient which clip if contacting the skin could cause ancillary irritation.

All of these disadvantages of procedure for bandaging a mastectomy patient or a patient having chest surgery are overcome by the present invention which does not introduce further disadvantages.

In accordance with the present invention, there is provided an improved surgical chest dressing comprising a chest encircling flexible band formed primarily from a stretchable material. This band has a longitudinally continuous back portion adapted to lie against the back of a person using the dressing. The continuous back portion has two longitudinally spaced ends with each of the ends connected to one of a pair of front flaps. These front flaps include free ends spaced from the back portion and overlapping each other at engaging surfaces when the dressing is wrapped around a patient using the same. A two element, contact sensitive, reusable fastening means for releasably securing the free ends together in selected, adjustable longitudinal positions is provided for closing the bandage around the patient.

One element of the fastening means is secured onto each of the engaging surfaces of the free ends of the front flaps. The first and second straps are provided with each of the straps being fixedly secured onto the back portion and adjustably secured onto the front flaps after the front flaps have been closed by the contact sensitive, reusable fastening means.

In accordance with the preferred embodiment of the present invention, the contact sensitive, reusable fastening means are "velcro" fasteners which are disclosed in U.S. Pat. No. 2,717,437. This patent is incorporated by reference herein and includes a disclosure of a fastening means including a gripping strip having a number of small, outwardly extending, closely spaced flexible hooks which hooks engage the strands of a loosely knitted, velvet type fabric by a transvers engagement of the strip having the hooks with the velvet-like fabric. This type of fastening means is well known and involves no metal elements. In addition, the fastening means is infinitely variable in that the gripping strip including the hooks can be positioned at various locations on the fabric strip to adjust the position of the two flaps of the strips with respect to each other.

In accordance with another aspect of the invention, the straps extending from the back portion of the dressing to the front flaps extends through loops on the front flaps and back upon themselves.

At the point of rejoining the straps, another "velcro" fastening arrangement is provided. This second fastening means on the two straps includes a first element at the loose end of the strap and a second element on the body of the strip which may be adjacent the back portion. By moving the straps through the loops and back upon themselves, an infinitely adjustable length for the straps is possible.

By adopting an improved surgical chest dressing of the type described above, the back portion of the dressing may be slipped under the patient without disrupting anesthetic apparatus or any intravenous needles. After a dressing is placed over the closed incision, the dressing is closed in the front and drawn snug by a proper closing of the front flaps with the variable fastening means. Thereafter, each of the straps extending from the back portion can be slipped through the loops on the front flaps and back upon themselves and adjusted to the proper position to match the contour of the patient. In this manner no metallic clips are required, an infinitely variable bandage is provided, and the patient need not be disturbed while the dressing is being applied. The dressing is variable in size because of the fastening means used. In addition, the flexible band extending around the chest of the patient is formed from a stretchable material which stretches in all directions to conform with both the natural breast and the dressing on the patient's closed incision. The term "stretchable" is distinguished from elastic in that a stretchable material conforms to the body shape without exerting substantial pressure. An elastic material has a higher and more pronounced return capability so that when elongated, a returning force is exerted which returning force is quite high and proportional to the amount of elongation.

In the fabric art, the difference between stretchable and elastic fabrics are well known. The elastic fabrics tend to bind and exert confining pressure.

In accordance with another aspect of the invention, the front flaps are provided with two stretchable portions sewed together to provide an outwardly protruding profile which will accommodate the dressing and the natural breast when the bandage is used for a mastectomy patient.

In use of this dressing, a mastectomy patient feels that she is wearing a brassiere. This assists in the post-operative emotional strain which can be associated with a mastectomy. It has been found that patients using this improved dressing have been extremely pleased and have asked to wear the dressing when leaving the hospital for post-operative convalescence.

In addition, the dressing allows easy changing of the absorbent dressing on the closed incision by merely opening the front of the dressing and replacing the absorbent dressing over the incision. This can be done without lifting the patient and quite rapidly by a nurse or other attendant. The improved chest dressing or bandage explained above also provides sufficient support for the unoperated breast and does not distort the breast during postoperative convalescence by the patient. All of these advantages are extremely important to a person who has experienced the trauma of a mastectomy operation.

The primary object of the present invention is the provision of a surgical chest dressing which provides proper support for the absorbent dressing and still is acceptable and comfortable to the patient.

Yet another object of the present invention is the provision of a surgical chest dressing that can be applied to a patient of either sex in the operating room while the patient is still under the influence of an anesthesia without disturbance of the anesthetic equipment, the position of the arms of the patient or any other equipment connected to the patient during the operating procedure.

Another object of the present invention is the provision of a surgical chest dressing that can be conveniently placed under the back of a patient while on the operating table and closed from the front without using metallic clips or elastic bandaging.

Another object of the present invention is the provision of an improved dressing as defined above which does not restrict the patient's respiration or cause skin irritation due to the existence of metal clips or clamps.

Yet another object of the present invention is the provision of a dressing as defined above, which dressing allows for the changing of the dressing with a minimum inconvenience of the patient.

Still a further object of the present invention is the provision of a surgical chest dressing which can be used on a mastectomy patient without distorting the unoperated breast during the postoperative convalescence.

Yet another object of the present invention is the provision of a surgical chest dressing as defined above, which dressing is inexpensive to produce and can be applied to the patient with a minimum of patient disturbance and a minimum of time.

These and other objects and advantages will become apparent from the following description taken together with the accompanying drawings in which.

Figure 1:
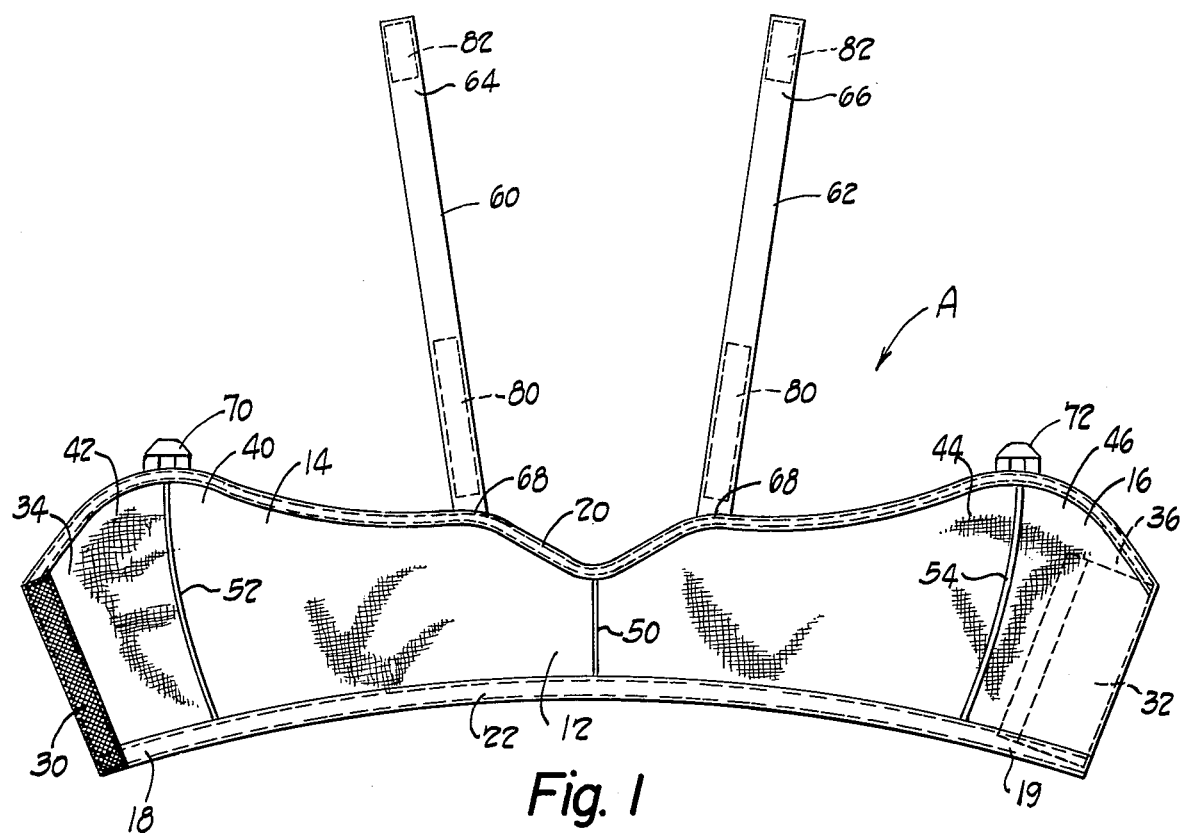
FIG. 1 is a plan view of the inner face of the surgical chest dressing constructed in accordance with the preferred embodiment of the present invention and shown in fully opened condition.
Figure 2:
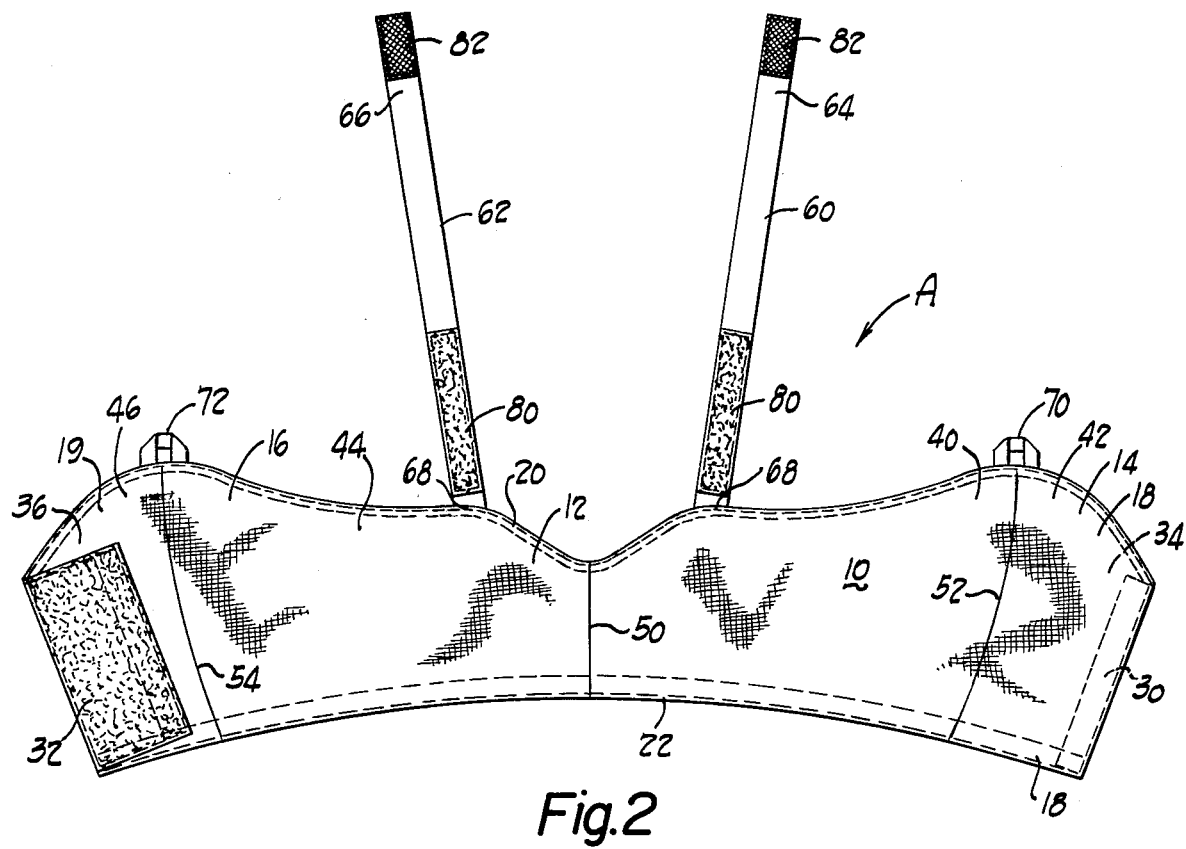
FIG. 2 is a plan view of the outer face of the preferred embodiment and again shown in a fully opened condition.
Figure 3:
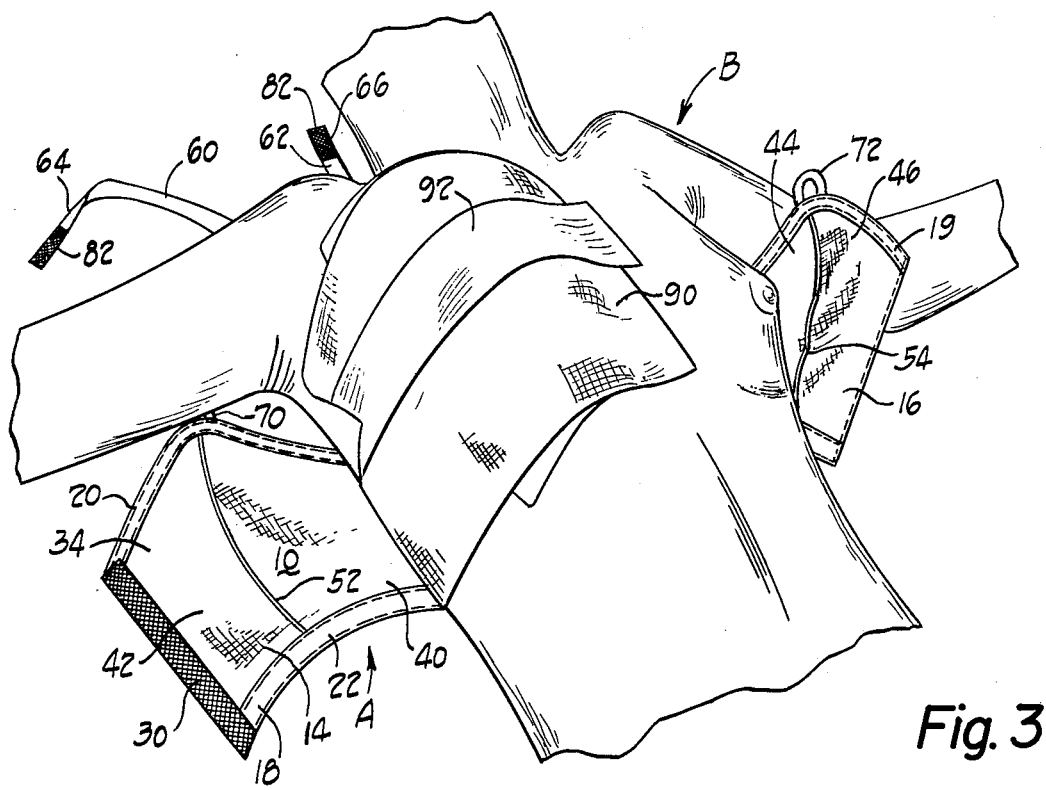
FIG. 3 is a perspective view showing a patient in a reclining position after a breast operation, with a gauze bandage or dressing in place over the closed incision of a mastectomy operation and with the preferred embodiment of the invention extending under the patient's back in an open condition preparatory to front closing.
Figure 4:
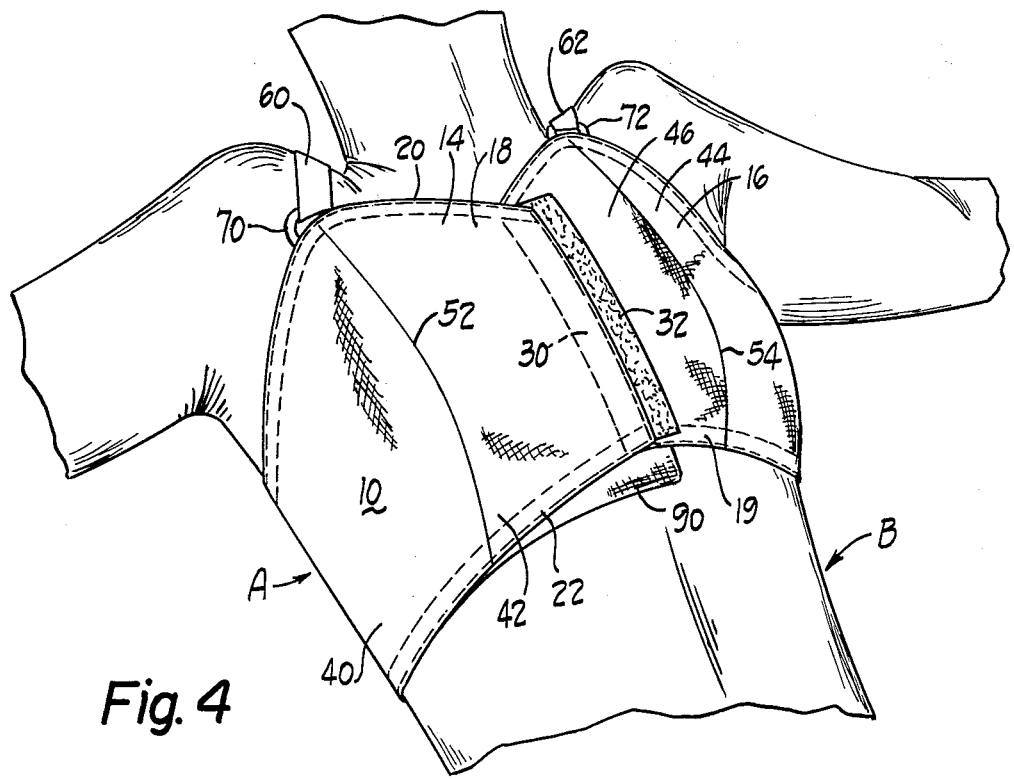
FIG. 4 is a perspective view similar to that shown in FIG. 3 illustrating the closed condition of the preferred embodiment of the present invention; and, FIG. 5 is a perspective view of the preferred embodiment of the present invention in the closed position and with certain cut away portions with the body of the patient shown in FIG. 4 omitted for simplicity.
Figure 5:
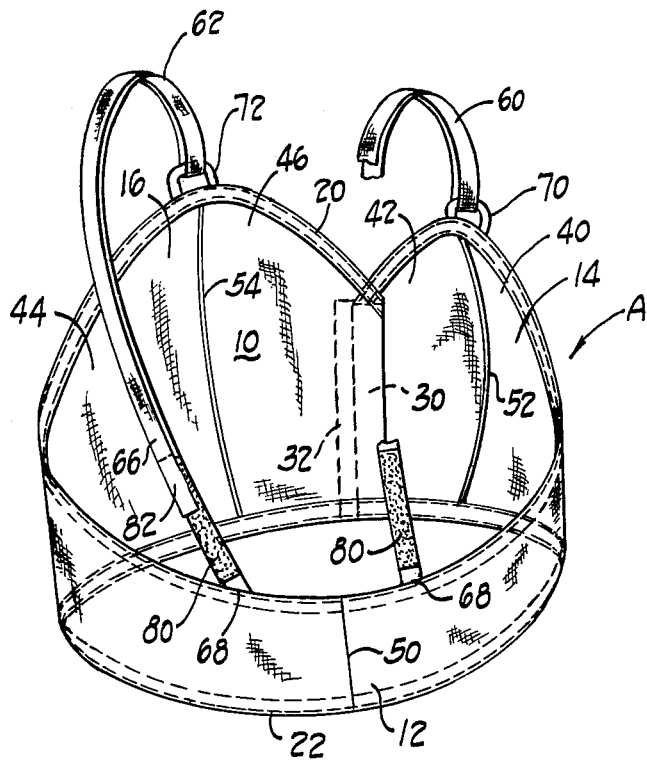

Referring now to the drawings wherein the showings are for the purpose of illustrating a preferred embodiment of the invention only, and not for the purpose of limiting same, FIGS. 1 and 2 show a surgical chest dressing A for use around the chest of an operative patient B as shown in FIGS. 3 and 4.

In accordance with the preferred embodiment of the invention, chest dressing A which may be referred to as a bandage, includes a flexible band 10 formed primarily from a stretchable, but non-elastic fabric or material. This definition is well known in the art and in practice is a loose weave, porous 100% knit Nylon which allows freedom of movement of the material in all directions and a low recovery force so that the material does not exert substantial pressure on the patient during use of the dressing or bandage. Flexible band 10 includes a back engaging portion 12 which is longitudinal and continuous without fasteners or other coupling devices. Although band 10 is preferably stretchable material throughout its length, it is possible to provide certain areas with other material without departing from the intent of the invention. The extended ends of back portion 12 merge into two joined front flaps 14 and 16 having free ends 18, 19 which overlap when the dressing or bandage is in place around a surgical patient. An undulating upper marginal strip 20 is provided around the upper portion of flexible band 10. In a like manner, a generally straight lower marginal band 22 is provided along the lower portion of flexible band 10. These two marginal strips are formed from elastic material which provides the strength for the bandage or dressing in the longitudinal direction so that the bandage holds the general shown in FIGS. 1 and 2. The free ends 18, 19 overlap in the front when the bandage or dressing A is in place around a postoperative patient.

The overlapping surfaces of these free ends are provided with a two element, contact sensitive, reusable fastening means to provide infinitely selected longitudinal positions within a given general range determined by the elements forming the fastening means. Means include no metal elements and is, in the preferred embodiment, a Velcro fastener wherein the first element 30 is a transversely extending gripping strip including a number of small, outwardly extending, closely spaced flexible hooks which take on the appearance of a rough fabric. The second element 32 is a fabric strip extending transversely of flexible band 10 and interlocks with the hooks of gripping strip 30. This second element assumes the normal appearance of a velvet fabric. Strips 30, 32 are non-elastic and non-stretchable to provide transverse stability for bandage or dressing A. These strips extend between the elastic strips 20, 22 to complete the boundary for the bandage and provide the final dimensional stability and general strength for the bandage. The overlapping surfaces onto which elements 30, 32 are provided are designated 34, 36, respectively, in FIGS. 1 and 2. These overlapping surfaces are at the free ends 18, 19 of front flaps 14, 16.

Referring now more particularly to the front flaps 14, 16, these flaps are formed by two separate pieces of stretchable material. Front flap 14 includes pieces 40, 42, while front flap 16 includes pieces 44, 46. Thus, the internal structure of flexible band 10 includes four separate stretchable, non-elastic panels. The panels 40, 44 are joined at the back portion 12 by a transverse seam 50 which is loosely sewn to allow normal transverse stretching of the pieces or panels 40, 44. Of course, in some instances panels 40, 42 could be a continuous longitudinally extending panel.

Pieces or panels 40, 42 are joined together by a seam 52. In a like manner, panels 44, 46 are joined together by a seam 54. Seams 52, 54 are longer than the non-stretched, transverse dimension so that forwardly extending profiles are created at the forward portions of front flaps 14, 16. This forward contour allows better conformity to the under dressing on a closed incision and on the non-operated breast of a mastectomy patient. In some instances, seams 52, 54 may be eliminated and a single panel used in forming the front flaps 14, 16.

As so far described, flexible band 10 can be wrapped around a post surgical patient and connected at the front by strips 30, 32. Strips are secured together by engaging strip 30 at a selected position on strip 32. To support the dressings or bandage on the postoperative patient, two spaced straps 60, 62 are provided. These straps include loose ends 64, 66, respectively and are secured by seams 68 to back portion 12 of band 10. This is a fixed fastening arrangement so that no manipulation is needed under the patient when bandage of dressing A is applied around a surgical patient while on the operating table as shown in FIG. 3. Straps 60, 62 are adjustably secured to the front flaps 14, 16 by an appropriate fastening arrangement which involves no metal clips and can be easily done to adjust the proper position of the bandage while the patient is still on the operating table. In accordance with the preferred embodiment, front flaps 14, 16 include loops 70, 72, respectively. These loops are formed from non-elastic, non-stretchable cloth and are secured onto elastic marginal strip 20 adjacent the larger transverse dimension of band 10. To fasten the strips in an effective adjusted length, the loose ends 64, 66 are passed through loops 70, 72. Fastening strips 80, 82 on each strap are again Velcro fasteners with one strip including the hooks and the other strip including the engaging fabric. In the illustrated embodiment, strips 80 are formed from the engaging fabric and strips 82 include the small gripping hooks used in a Velcro fastener.

Referring now to FIG. 3, a mastectomy surgical patient B is illustrated in the reclining position with arms extended. An absorbent dressing 90 is placed over the closed incision and tape 92 lightly holds the absorbent dressing in place. Thereafter, the present invention is placed under the patient as shown in FIG. 3 with the back portion engaging the back of the patient and front flaps 14, 16 extending loosely to either side generally under the arms. Thereafter, the front flaps are brought together and snugly secured by elements 30, 32 in front of the patient as shown in FIG. 4. Loose ends 64, 66 are brought over the shoulders of the patient and passed from the back through loops 70, 72. Loose ends 64, 66 are then folded back on straps 60, 62 and strips 82 engage strips 80. This provides a snug fit over the shoulder of the patient without disturbing the position of the patient or any apparatus being used in the operation procedure. Thereafter, the patient is ready for convalescence To change dressing 90, it is only necessary to loosen the straps and open the front of bandage or dressing A. This can be done quite easily by a relatively untrained person. By providing the stretchable, non-elastic material in band 10, respiration of the patient is unaffected and undue pressure is not exerted on the bandage 90. In addition, the non-operated breast is supported but not distorted.

It will now be clear that there has been provided a device which accomplishes the objectives heretofore set forth.

While the invention has been disclosed in its preferred form, it is to be understood that the specific embodiment thereof, as described and illustrated herein, is not to be considered in a limited sense, as there may be other forms or modifications of the invention which should also be construed to come within the scope of the appended claims.

I claim:

1. A surgical chest dressing comprising: a chest encircling flexible band formed primarily from a stretchable material, said band having a longitudinally continuous back portion adapted to lie against the back of a person using said dressing; said continuous back portion having two longitudinally spaced ends, with each of said ends connected to one of a pair of front flaps; said front flaps including free ends spaced from said back portion and overlapping each other at engaging surfaces when said dressing is wrapped around a person using the same; a two element, contact sensitive, reusable fastening means for releasably securing said free ends together in selected, adjustable longitudinal positions with one element of said fastening means being secured to each of said engaging surfaces of said free ends; first and second straps, each of said straps being fixedly secured onto said back portion; and, means on each of said front flaps for securing one of said straps thereto.

2. A surgical chest dressing as defined in claim 1 wherein each of said front flaps has a non-stretched transverse dimension at a position adjacent said strap securing means and including two stretchable material panels joined together at said position with a seam which is substantially greater than said transverse dimension whereby said front flaps can assume a non-stretched outwardly protruding profile.

3. A surgical chest dressing as defined in claim 1 wherein said stretchable material is stretchable in all directions.

4. A surgical chest dressing as defined in claim 1 wherein one of said elements of said contact sensitive, reusable fastening means is a gripping strip including a number of small, outwardly extending, closely spaced flexible hooks and said other of said elements is a fabric strip into which said hooks are releasably engaged by contact of said gripping strip with said fabric strip.

5. A surgical chest dressing as defined in claim 1 wherein said flexible band includes upper and lower longitudinally extending elastic marginal body engaging bands to define outer engaging surfaces for said dressing.

6. A surgical chest dressing as defined in claim 1 wherein said straps have loose ends and said front flap has an upper portion, said strap securing means on each of said front flaps includes a loop secured to said front flap at said upper portion thereof, a first fastener element secured onto said strap at a position spaced from said loose end and a second fastening element secured onto said strap adjacent said loose end whereby said loose end may be passed through said loop and said second element fastens onto said second element, said first and second elements being fastenable at variable positions to adjust the effective length of said strap.

7. A surgical chest dressing as defined in claim 6 wherein said first and second fastening elements are joinable in infinitely variable positions.

8. A surgical chest dressing as defined in claim 7 wherein said first element is a gripping strip including a number of small outwardly extending, closely spaced flexible hooks and said second element is a fabric strip into which said hooks are releasably engaged by contact of said gripping strip with said fabric strip.

9. A surgical chest dressing as defined in claim 8 wherein said stretchable material is stretchable in all directions.

10. A surgical chest dressing as defined in claim 8 wherein one of said elements of said contact sensitive, reusable fastening means is a gripping strip including a number of small, outwardly extending, closely spaced flexible hooks and said other of said elements is a fabric strip into which said hooks are releasably engaged by contact of said gripping strip with said fabric strip.

* * * * *